(12) United States Patent
Fabien

(10) Patent No.: US 12,303,663 B2
(45) Date of Patent: May 20, 2025

(54) FLUID INJECTION DEVICE

(71) Applicant: APTAR FRANCE SAS, Le Neubourg (FR)

(72) Inventor: David Fabien, Corseul (FR)

(73) Assignee: APTAR FRANCE SAS, Le Neubourg (FR)

( * ) Notice: Subject to any disclaimer, the term of this patent is extended or adjusted under 35 U.S.C. 154(b) by 1165 days.

(21) Appl. No.: 17/259,783

(22) PCT Filed: Jul. 11, 2019

(86) PCT No.: PCT/FR2019/051742
§ 371 (c)(1),
(2) Date: Jan. 12, 2021

(87) PCT Pub. No.: WO2020/012128
PCT Pub. Date: Jan. 16, 2020

(65) Prior Publication Data
US 2021/0196883 A1    Jul. 1, 2021

(30) Foreign Application Priority Data

Jul. 13, 2018   (FR) ........................................ 1856472

(51) Int. Cl.
*A61M 5/14*    (2006.01)
*A61M 5/142*   (2006.01)

(52) U.S. Cl.
CPC ...... *A61M 5/1408* (2013.01); *A61M 5/14228* (2013.01); *A61M 2005/1402* (2013.01); *A61M 2205/52* (2013.01); *A61M 2205/8206* (2013.01)

(58) Field of Classification Search
CPC ............ A61M 5/1408; A61M 5/14228; A61M 2005/1402; A61M 2005/52; A61M 2005/8206
See application file for complete search history.

(56) References Cited

U.S. PATENT DOCUMENTS 2,954,028 A * 9/1960 Smith ................ A61M 5/1408
                                                            137/271
3,140,666 A * 7/1964 Currie ................ F04B 43/1284
                                                            417/477.11
(Continued)

FOREIGN PATENT DOCUMENTS

EP     1 541 184 A1    6/2005
EP     2 179 754 A1    4/2010
(Continued)

OTHER PUBLICATIONS

International Search Report for PCT/FR2019/051742, dated Oct. 22, 2019.
(Continued)

*Primary Examiner* — Nathan R Price
*Assistant Examiner* — Mark A Igel
(74) *Attorney, Agent, or Firm* — Sughrue Mion, PLLC

(57) ABSTRACT

A fluid injection device having a body contacting an injection site (SI); fluid reservoirs (210); an injection needle (120) that injects the contents of the reservoir(s) (210); and a respective priming needle (125) associated with each reservoir (210) for penetrating into the reservoir (210) before dispensing the fluid. Each reservoir (210) includes a tube (145) connected at one end to a priming needle (125), and at the other end to the injection needle. The device includes a reservoir selector for selecting one or more reservoirs (210), the contents of which are dispensed during the next actuation. The selector has a rotary member (132, 135) with a cam (1320, 1350) to co-operate with the tubes (145) so as to open or close the flow of fluid through each tube (145).

25 Claims, 11 Drawing Sheets

(56) References Cited

U.S. PATENT DOCUMENTS

| | | | | | |
|---|---|---|---|---|---|
| 3,477,469 | A | * | 11/1969 | Paley | A61M 5/1408 137/883 |
| 3,941,126 | A | * | 3/1976 | Dietrich | A61M 5/1408 604/250 |
| 3,957,082 | A | * | 5/1976 | Fuson | A61M 39/223 604/80 |
| 4,237,880 | A | * | 12/1980 | Genese | A61M 5/36 137/859 |
| 4,909,710 | A | * | 3/1990 | Kaplan | F04B 43/082 417/474 |
| 5,660,529 | A | * | 8/1997 | Hill | F04B 43/082 417/474 |
| 2006/0167415 | A1 | * | 7/2006 | Nemoto | A61M 5/1456 604/154 |
| 2007/0088271 | A1 | * | 4/2007 | Richards | A61M 5/14244 604/890.1 |
| 2011/0004187 | A1 | * | 1/2011 | Beiriger | A61M 5/162 604/500 |
| 2012/0022494 | A1 | * | 1/2012 | Kirkpatrick | A61M 5/16827 604/151 |
| 2014/0288423 | A1 | * | 9/2014 | Yamamoto | A61M 5/007 600/432 |

FOREIGN PATENT DOCUMENTS

| | | | | |
|---|---|---|---|---|
| EP | 2 283 885 | A1 | 2/2011 | |
| JP | 2004290455 | A * | 10/2004 | A61M 5/1407 |
| JP | 4515037 | B2 * | 7/2010 | A61M 5/1407 |
| JP | 2011217816 | A * | 11/2011 | |
| JP | 5586310 | B2 * | 9/2014 | |
| JP | 6510490 | B2 * | 5/2019 | A61M 39/223 |
| JP | 6873026 | B2 * | 5/2021 | A61J 1/20 |
| WO | WO-9736623 | A1 * | 10/1997 | A61M 5/14232 |
| WO | 2012/085428 | A1 | 6/2012 | |
| WO | WO-2013153812 | A1 * | 10/2013 | A61M 5/145 |
| WO | 2013/171311 | A1 | 11/2013 | |
| WO | WO-2014062160 | A1 * | 4/2014 | A61M 39/285 |
| WO | WO-2015141202 | A1 * | 9/2015 | A61M 39/223 |

OTHER PUBLICATIONS

International Preliminary Report on Patentability dated Jan. 14, 2021, in International Application No. PCT/FR2019/051742.

* cited by examiner

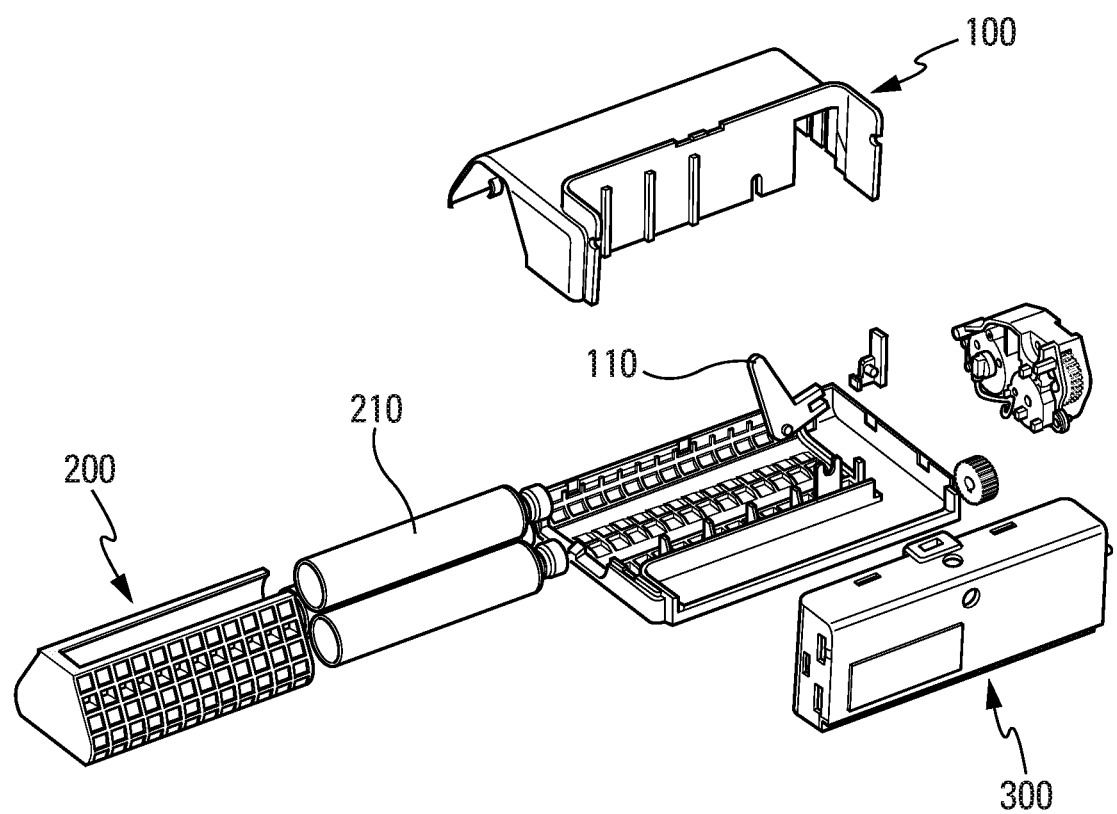
Fig. 1
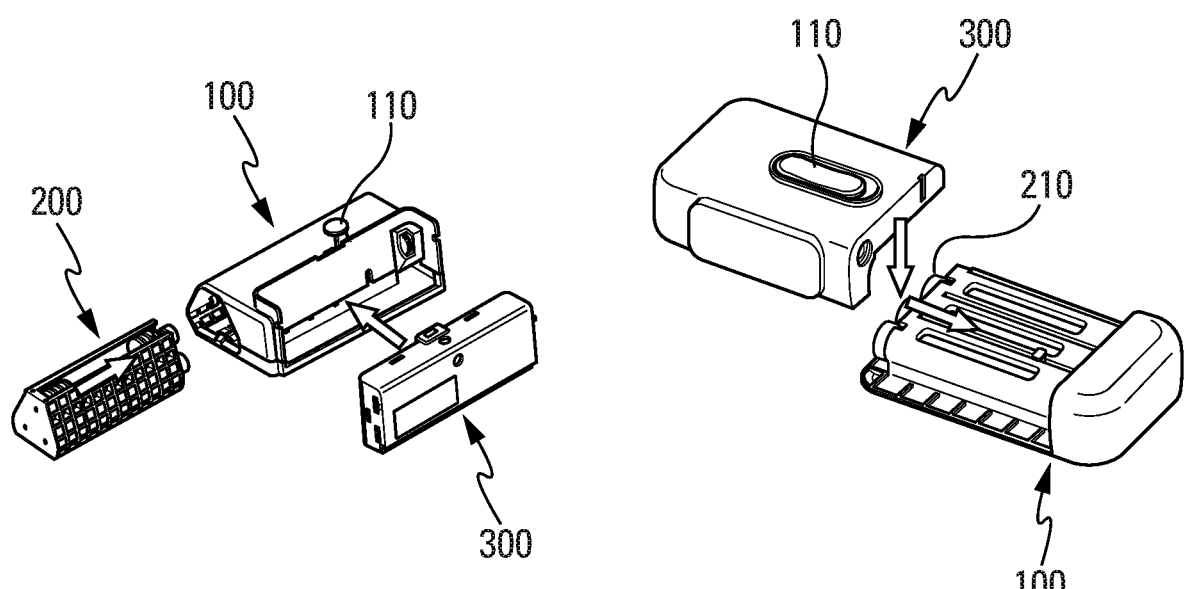
Fig. 2a
Fig. 2b

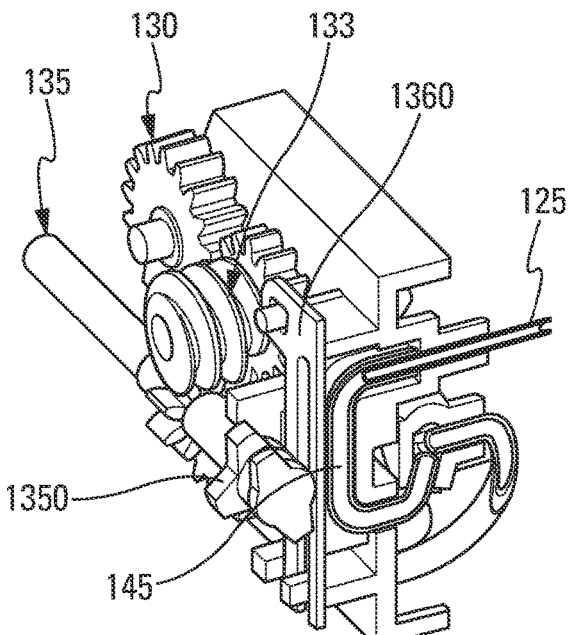
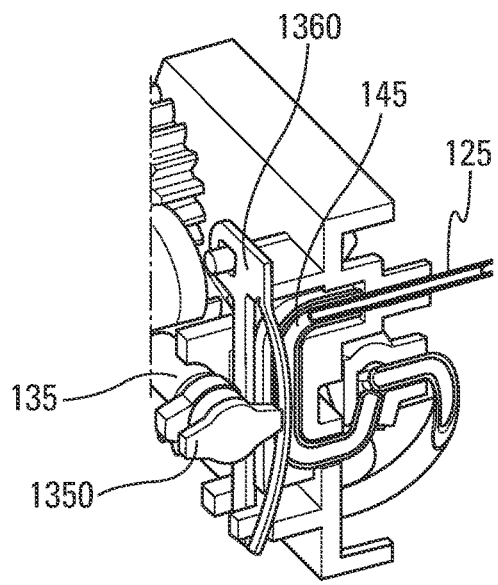
Fig. 32  Fig. 33
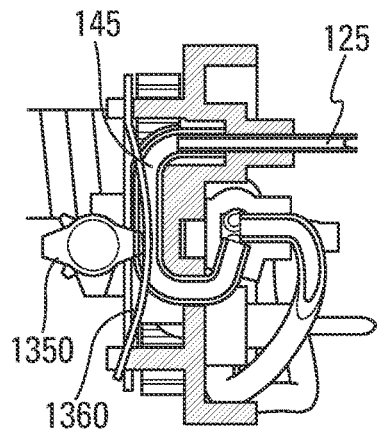 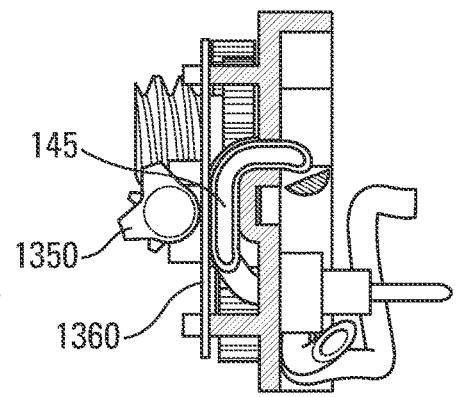 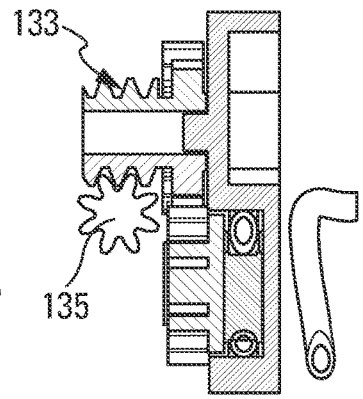
Fig. 34  Fig. 35  Fig. 36
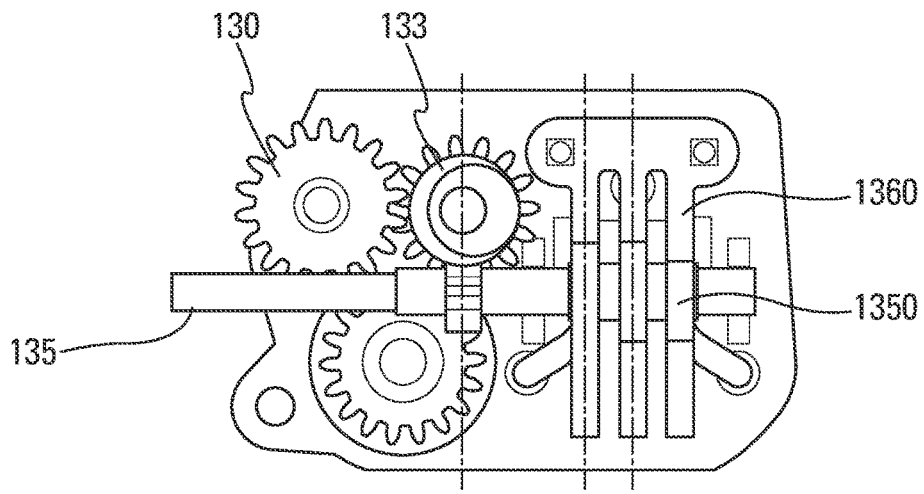
Fig. 37

FLUID INJECTION DEVICE

This application is a National Stage of International Application No. PCT/FR2019/051742 filed Jul. 11, 2019, claiming priority based on French Patent Application No. 1856472 filed Jul. 13, 2018.

The present invention relates to a fluid injection device.

Fluid injection devices are well known. In particular, they include autoinjectors in which the contents of a reservoir, generally a syringe, are automatically injected by means of an actuator system that generally includes a loaded spring, and that, on being triggered, moves a piston in the reservoir so as to inject the fluid.

Such prior-art devices can present problems, in particular when the volumes to be dispensed are large, when the fluid is relatively viscous, or when a plurality of fluids needs to be combined in a single treatment. Thus by way of example, injectors of viscous fluids are generally not very compact, heavy, and voluminous, in particular when they contain a plurality of reservoirs. Furthermore, the fluid(s) contained in the reservoir(s) is/are generally in contact with numerous different materials between the outlet of the reservoir and the injection needle, which may present risks of potential contamination of the fluid. In addition, although such devices are complex and often incorporate electronics, they are generally disposed of in their entirety after use.

Documents JP 2004/290455, EP 1 541 184, WO 2012/085428, WO 2013/171311, EP 2 283 885, EP 2 179 754, and US 2007/088271 describe prior-art devices.

An object of the present invention is to provide an injection device that does not have the above-mentioned drawbacks.

Another object of the present invention is to provide an injection device that makes it possible to dispense fluid, even at large volumes and/or high viscosities.

Another object of the present invention is to provide a fluid injection device that is compact and not very bulky.

Another object of the present invention is to provide a fluid injection device that includes a portion that can be reused and/or recycled separately.

Another object of the present invention is to provide a fluid injection device that ensures that the fluid to be dispensed comes into contact with the smallest possible number of different materials, all adapted to convey pharmaceutical fluid.

Another object of the present invention is to provide a fluid injection device that is simple and inexpensive to manufacture and to assemble.

The present invention thus provides a fluid injection device comprising: a body for coming into contact with an injection site; at least three fluid reservoirs; an injection needle for penetrating into said injection site so as to inject therein the contents of one or more reservoir(s); and a respective priming needle associated with each reservoir for penetrating into said reservoir before dispensing the fluid, each reservoir including a tube that is connected at one end to its priming needle, and at the other end to said injection needle; said device further comprising reservoir selector means for selecting one or more reservoirs, the contents of which are to be dispensed during the next actuation, said selector means comprising a rotary member that is provided with cam means that are adapted to co-operate with the tubes of the reservoirs so as to open or close the flow of fluid through each tube, the flow of fluid in a tube being closed off by said cam means pinching/flattening said tube.

In a first advantageous embodiment, said rotary member is a selector cog provided with a cam.

Advantageously, said cam is formed by a projection that is circularly arcuate, said cam being interrupted by at least one gap, such that when said cam is in contact with a tube it pinches it so as to cut off the flow of fluid, and when a tube is situated facing said gap it is possible for fluid to flow.

In a variant, said cam is formed in radial manner in a central hole of said selector cog, said tubes passing through said central hole, said cam including a larger-diameter portion, such that when a tube co-operates with said cam it is pinched, and when a tube co-operates with the larger-diameter portion it is not pinched.

In a second advantageous embodiment, said rotary member is a selector shaft provided with cam elements.

Advantageously, said cam elements co-operate with a pinch member provided with a plurality of flexible blades, one for each reservoir tube, such that when a cam element deforms a flexible blade of the pinch member, said flexible blade pinches its respective tube so as to cut off the flow of fluid.

Advantageously, said pinch member is made as a single piece.

Advantageously, the device includes a peristaltic pump comprising a ring that is mounted to rotate on a crankshaft, said ring turning about an axis of rotation that is offset relative to the axis of rotation of said crankshaft, progressively compressing a portion of tube that extends around said crankshaft.

Advantageously, said ring turns about a central cylinder of said crankshaft.

Advantageously, said portion of tube is connected at one end to a manifold that receives the tubes of each reservoir, and at the other end to said injection needle.

Advantageously, the device includes a single rotary actuator that, when it turns in a first direction of rotation, activates the selection of the reservoir(s) to be dispensed, and that, when it turns in the opposite direction, actuates a dispenser system, in particular a peristaltic pump.

Advantageously, said actuator includes a central pin that extends through an oblong opening of the body, thereby forming a floating cog.

Advantageously, each reservoir has a fluid content in the range 1 milliliter (mL) to 10 mL, advantageously about 3 mL.

Advantageously, said device includes an electronic module.

Advantageously, said electronic module comprises: a power supply, in particular an optionally rechargeable battery; a microprocessor; storage means; signal transceiver means; and a motor.

Advantageously, said electronic module is reusable and is assembled in removable manner on the device.

These and other characteristics and advantages appear more clearly from the following detailed description, given by way of non-limiting example, and with reference to the accompanying drawings, in which:

FIG. 1 is an exploded diagrammatic perspective view of an automatic injection device in an advantageous embodiment;

FIG. 2a is a diagrammatic perspective view similar to the view in FIG. 1, shown during assembly;

FIG. 2b is a diagrammatic perspective view similar to the view in FIG. 2a, showing a variant embodiment;

FIG. 6 is a diagrammatic and fragmentary exploded view in perspective of a selector module in an advantageous embodiment;

FIGS. 32 and 33 are diagrammatic and partially cut-away perspective views showing how the selector module in FIGS. 30 and 31 operates;

FIGS. 34 to 36 are diagrammatic and fragmentary section views showing how the selector module in FIGS. 30 and 31 operates;

FIG. 37 is a diagrammatic section view similar to the view in FIG. 31;

Figure 3:
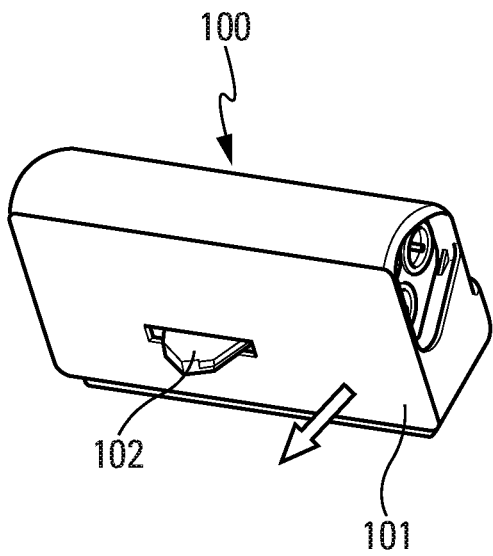
FIG. 3 is a diagrammatic perspective view similar to the view in FIG. 2, shown after assembly and before use.

The invention relates to an injection device that is particularly adapted to dispense relatively large volumes of fluid, typically of the order of a few milliliters, typically in the range 1 mL to 10 mL, e.g. 3 mL. The device of the invention is also adapted to dispense fluids that are relatively viscous.

Advantageously, the device comprises a plurality of modules. Thus, in the example in FIGS. 1, 2a, 3, and 4, the device comprises a main module, referred to below as a selector module 100, a reservoir module 200, and an electronic module 300. The selector module 100 and the reservoir module 200 are preferably disposable, while the electronic module 300 is preferably reusable. In the variant in FIG. 2b, the selector module 100 and the reservoir module 200 form a single module.

In this embodiment, the reservoir module 200 comprises three reservoirs 210, advantageously arranged in a triangle, in particular so as to save space, but naturally any number of reservoirs could be provided, e.g. more than three reservoirs. The reservoirs 210 may contain medications that are identical or different. In the examples in FIGS. 2b and 38 to 41, the reservoirs 210 are three in number, and they are arranged side-by-side, not in a triangle. In conventional manner, each reservoir 210 may include a piston that, during actuation, is moved in said reservoir.

The use of a device having a plurality of reservoirs makes it possible in particular to provide the following advantages:

a single device for two or more types of fluid, which may require different volumes to be dispensed;

the possibility of dispensing cocktails or a mixture of two or more fluids;

the possibility of associating pain-reducing agents (anesthetics, acid neutralizers, etc.) together with the medication to be injected;

the possibility of having different medication treatment frequencies; e.g. a first sequence S1 of taking a plurality of different medications, followed by a second sequence S2 of taking a single medication, etc.;

the possibility of standardizing the injection device for several types of treatment;

a reduction in the cost of developing devices;

the possibility of adjusting the formulation of the fluid;

various fluid formulations can be housed in a single device; and a reduction in the number of injections.

Figure 4:
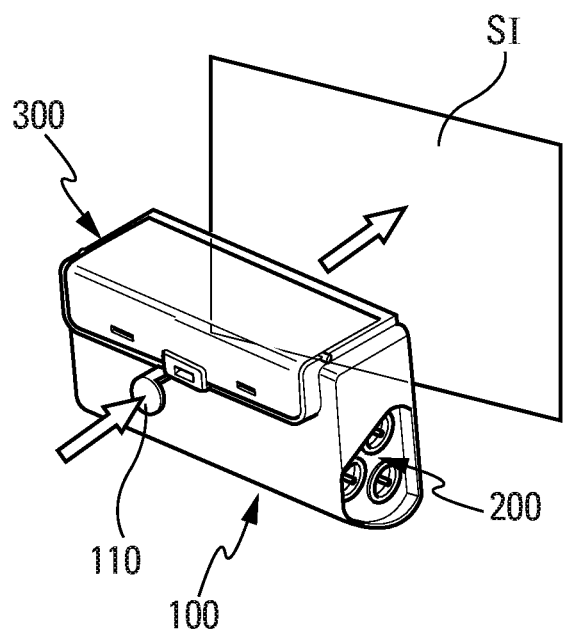
FIG. 4 is a diagrammatic perspective view similar to the view in FIG. 3, shown while being applied to the injection site.

FIGS. 2a, 3, and 4 show the successive steps during use of the device.

Thus, initially, the electronic module 300 and the reservoir module 200 are assembled on the selector module 100, as can be seen in FIG. 2a. It is possible to envisage initially assembling the electronic module 300, or, on the contrary, initially assembling the reservoir module 200. Advantageously, it is possible to envisage activating the electronic module 300 once it is assembled, so as to pass from "standby" or OFF mode in which it consumes little energy, if any, to an "active" mode in which it is ready to operate. Alternatively, the electronic module 300 may be activated during assembly of the reservoir module 200, when said reservoir module is assembled last. Optionally, as shown in FIG. 3, the device may include a sensor 102 in the surface that is applied against the injection site SI, so as to activate the electronic module only when the device is applied against said injection site SI.

In the variant in FIG. 2b, the device comprises only two modules, an electronic module 300, and a main module that combines both the selector module 100 and also the reservoir module 200.

When the device is assembled, the protective film 101 provided on the rear face of the selector module 100 is removed (FIG. 3), and the device is applied to the injection site SI (FIG. 4), where it is held by an adequate adhesive, in known manner.

The user then presses on an actuator button 110 of the selector module 100 or of the electronic module 300 so as to actuate the device and inject fluid into the injection site SI.

The device is advantageously controlled by the electronic module 300. In particular, the electronic module comprises: a power supply, in particular an optionally rechargeable battery; a microprocessor; storage means; and signal transceiver means.

Preferably, the device is independent, but it could be controlled remotely, by transmitting control instructions to the electronic module during actuation of the device, in particular concerning the selection and/or the sequence of the reservoir(s) to be dispensed, the dispensing speed, etc.

The electronic module advantageously controls a motor 350 that actuates the movable elements of the device so as to perform an actuation cycle.

The electronic means of the electronic module 300 are not described in greater detail herein, since although they participate in the operation of the device, they do not form essential characteristics of the device, and they could be made in any way that is well known to the person skilled in the art.

In a variant, it is possible to envisage a mechanical actuator system, e.g. using one or more springs, to actuate the device, instead of and replacing the electronic module.

At the end of injection, the device is removed from the injection site SI, the electronic module 300 is removed from the device, in particular so that it can be reused, and the selector module 100 and the reservoir module 200 are thrown away.

Figure 5:
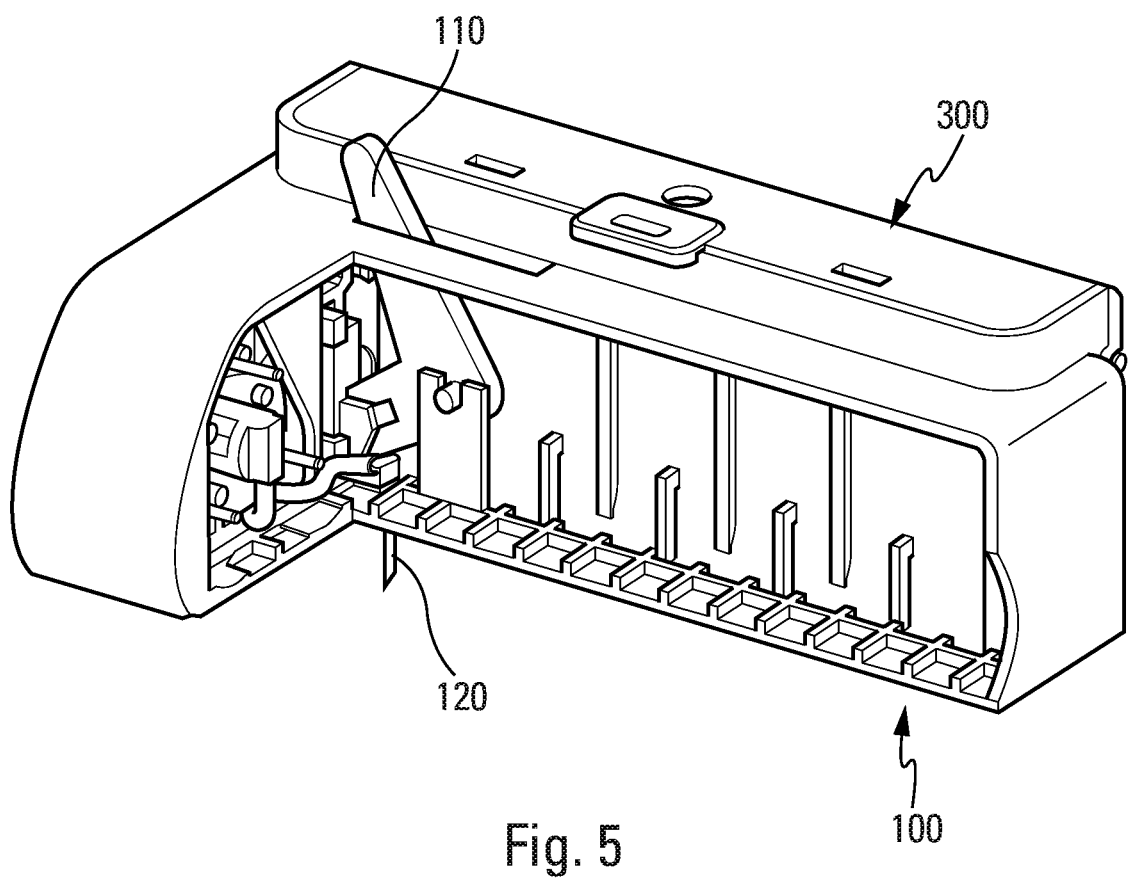
FIG. 5 is a diagrammatic and partially cut-away perspective view of the jabbing system of the injection needle.

FIG. 5 shows an example of an actuator button 110, in this embodiment in the form of a lever that pivots on the body of the selector module 100. Pivoting said lever firstly causes an injection needle 120 to be inserted into the injection site, and causes the device to be actuated so as to dispense fluid through said injection needle 120.

Advantageously, before actuation, the reservoir(s) 210 is/are closed by a septum-forming membrane, for piercing by a priming needle 125 during actuation. In the example shown in FIGS. 7 and 8, the selector module 100 includes three priming needles 125, one for each reservoir 210, for priming by piercing the membrane(s) when the reservoir module 200 is assembled in the selector module 100.

Figure 7:
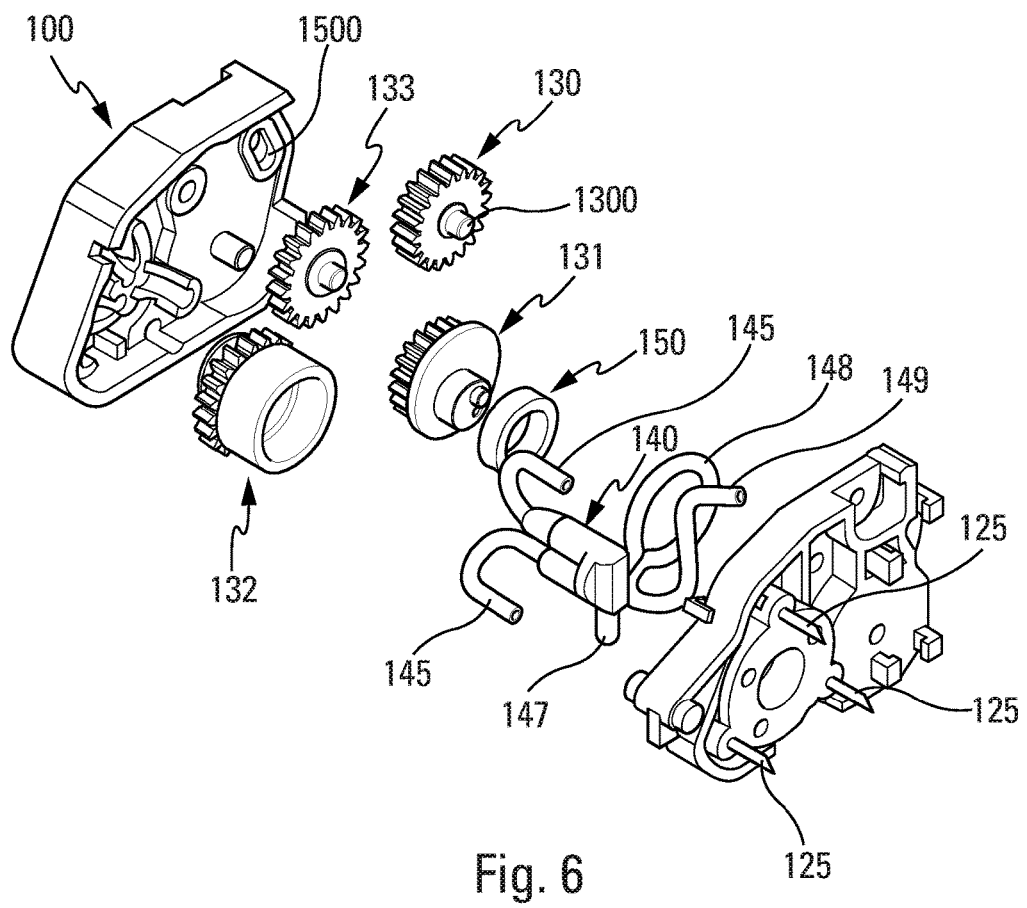
FIG. 7 is a diagrammatic and fragmentary perspective view of the FIG. 6 selector module.
Figure 8:
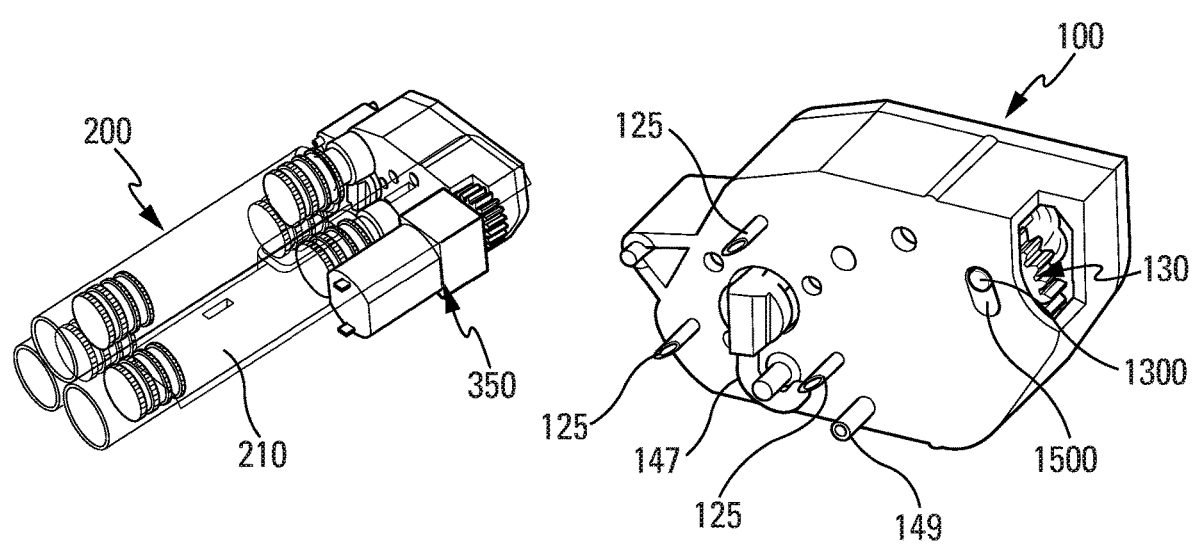
FIG. 8 is a diagrammatic and fragmentary perspective view of a reservoir module in an advantageous embodiment.
Figure 9:
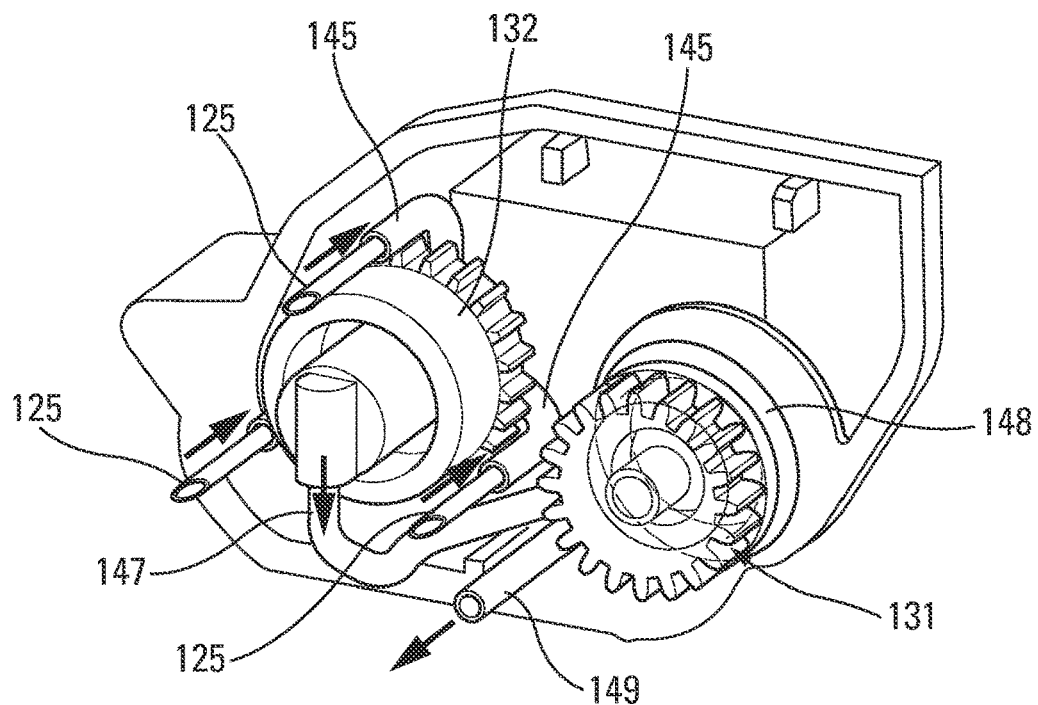
FIGS. 9 and 10 are diagrammatic and fragmentary perspective views showing, by transparency, how the selector module in FIGS. 6 and 8 operates.
Figure 10:
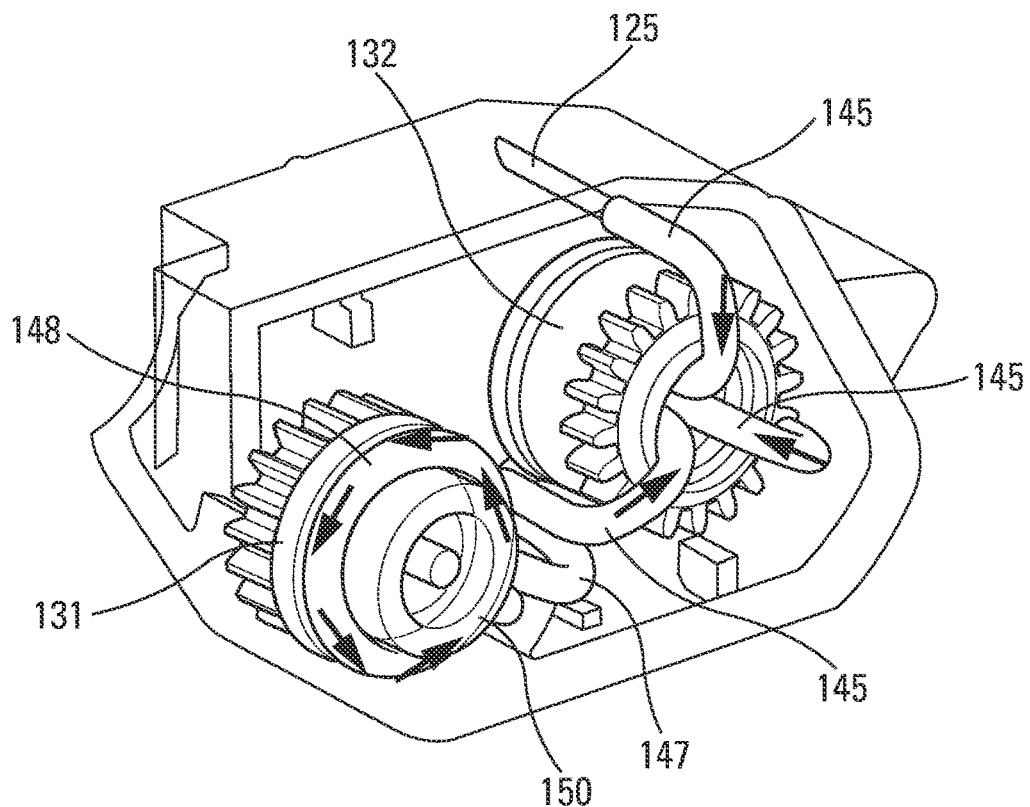

With a plurality of reservoirs 210, as shown in the example in FIGS. 7 and 8, the priming needles 125 of all of the reservoirs 210 are coupled to a single injection needle 120.

The selector module 100 is described with reference to several advantageous embodiments.

Advantageously, the selector module 100 operates as follows:
selecting the reservoir(s) 210 to be dispensed; and
dispensing the medication(s) contained in the selected reservoir(s) 210.

The reservoir(s) 210 is/are selected by pinching/closing off the tubes connected to each reservoir.

The contents of the selected reservoir(s) 210 are dispensed by means of a dispenser system, preferably in the form of a peristaltic pump 150, which is described more fully below with reference to FIGS. 18 to 23.

The selector module 100 advantageously includes a single rotary actuator 130 that is provided with a cog system 131, 132, 133, 134, 135. When the actuator 130 turns in a first direction of rotation, it activates selection of the reservoir(s) 210 to be dispensed, and when it turns in the opposite direction, it actuates the dispenser system, namely the peristaltic pump 150 in the example in FIGS. 18 to 23. Advantageously, it is the motor 350 of the electronic module 300, shown in FIG. 7, that turns said actuator 130.

The actuator 130 includes a central pin 1300 that extends through an oblong opening 1500 in the body of the selector module 100.

Depending on the direction of rotation of the actuator 130, the central pin 1300 shifts in translation from one end or the other of said oblong opening 1500.

Figure 26:
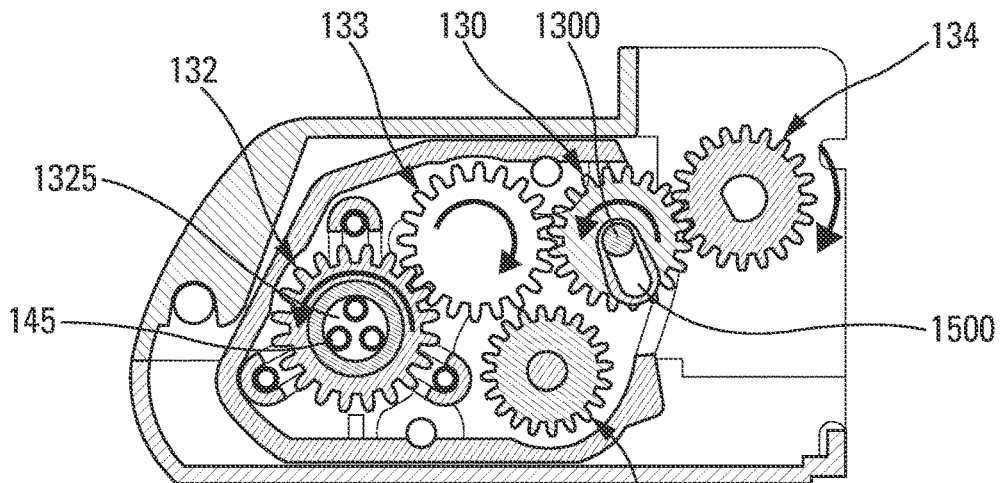
FIG. 26 is a diagrammatic section view of the floating cog of the FIG. 24 selector module, shown in selector mode.

At the first end, as can be seen in FIG. 26, the actuator 130 meshes with a selector cog 132, in particular via an intermediate cog 133, so as to actuate the selection of the reservoir(s) to be dispensed.

Figure 25:
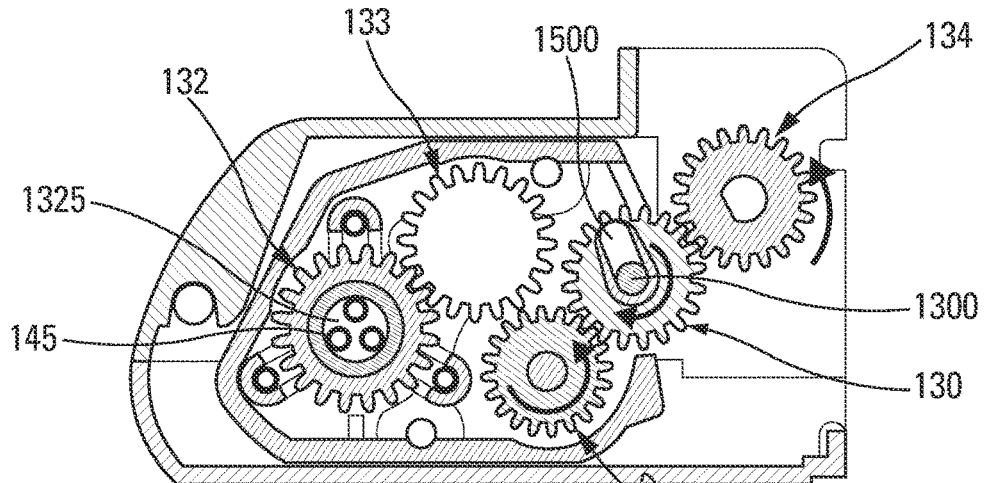
FIG. 25 is a diagrammatic section view of the floating cog of the FIG. 24 selector module, with the peristaltic pump being shown in its actuation mode.

At the other end, as can be seen in FIG. 25, the actuator 130 meshes with a crankshaft 131, so as to actuate the peristaltic pump.

In the examples in FIGS. 25, 26, and 38, 39, a drive cog 134 is provided so as to cause the actuator 130 to turn in one direction of rotation or the other. The drive cog 134 may be connected to the motor. In a variant, the drive cog could be omitted, and the motor could be connected directly to the actuator 130.

The actuator 130 is thus a floating cog. It is shifted in translation along the oblong opening 1500 as a function of its direction of rotation and as a result of the opposing torque from the other rotary elements described above.

The selector module 100 also advantageously includes a manifold 140 that includes respective tubes 145 coming from each of the reservoirs 210. Each tube 145 is connected at one end to its reservoir 210, and at the other end to the dispenser system, specifically in this embodiment to the peristaltic pump 150 and then the injection needle 120, via a set of tubes 147, 148, 149.

Figure 15:
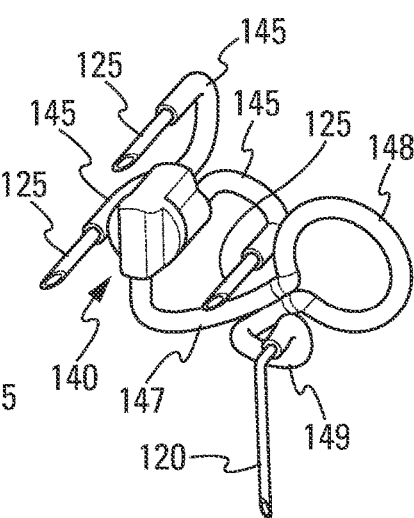
FIG. 15 is a diagrammatic and fragmentary perspective view of the tubing of the selector module in FIGS. 6 and 8.
Figure 30:
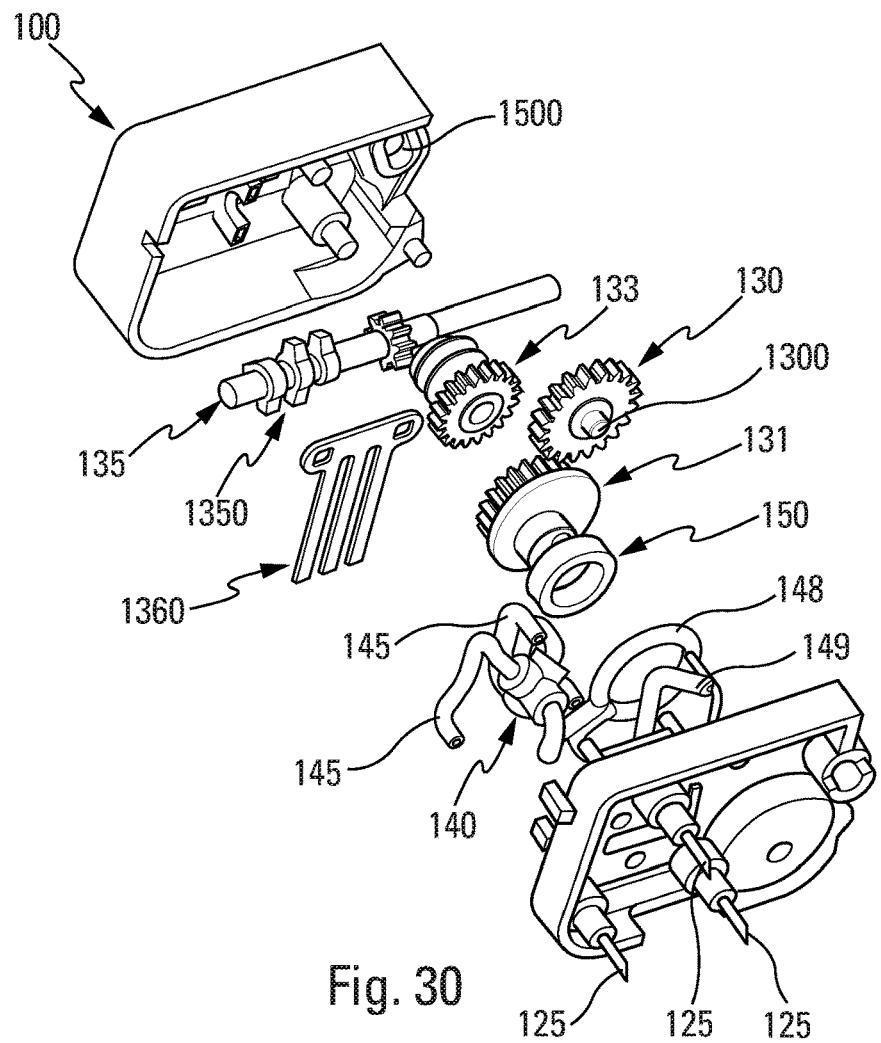
FIG. 30 is a diagrammatic and fragmentary exploded view in perspective of a selector module in yet another advantageous embodiment.
Figure 31:
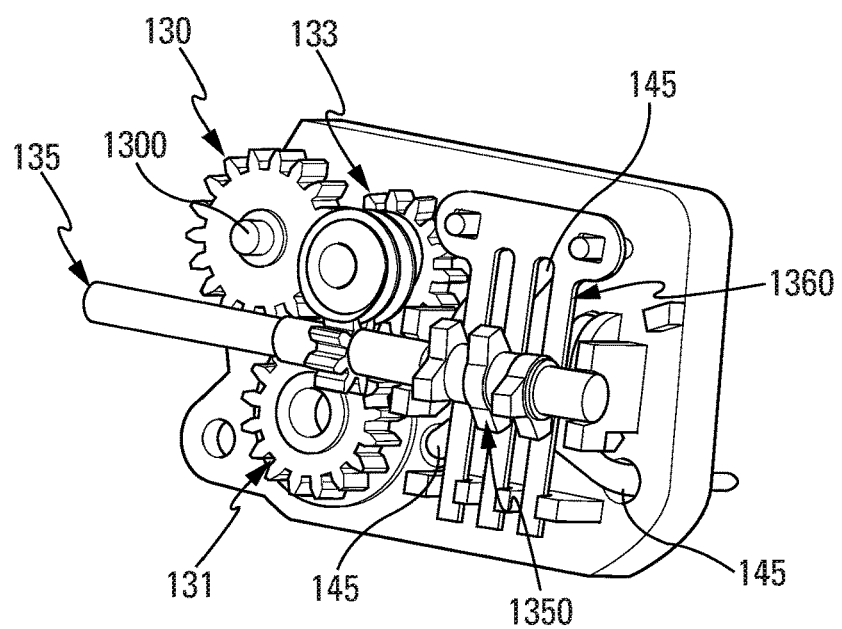
FIG. 31 is a diagrammatic and partially cut-away perspective view of the FIG. 30 selector module.
Figure 38:
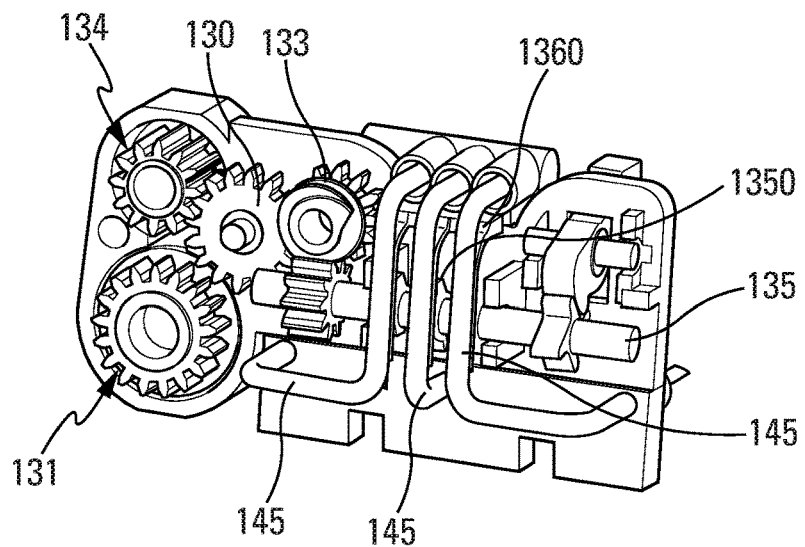
FIG. 38 is a diagrammatic and partially cut-away perspective view of a selector module in yet another advantageous embodiment.

With a plurality of reservoirs 210, in particular three reservoirs, as in the examples in the figures, the tubes 145 are joined together downstream from the dispenser system, so as to discharge into the injection needle 120. The set of tubes 145, 147, 148, 149 forms tubing, several variants of which are shown, in particular in FIGS. 6, 15, and 30.

Advantageously, the tube(s) 145, 147, 148, 149 are made out of a material that is compatible with the fluid(s) to be dispensed, e.g. materials commonly used to manufacture catheters.

The reservoir(s) 210 that is/are to be dispensed during actuation is/are advantageously selected by pinching or flattening one or more tubes 145 connected to the reservoirs 210. When a tube 145 is "pinched", the tube is closed off and fluid is prevented from flowing along the tube, and the contents of the corresponding reservoir 210 cannot flow towards the injection needle 120.

The tube(s) 145 is/are preferably pinched by cam means that are formed on a movable part, in particular a rotary member.

Figure 11:
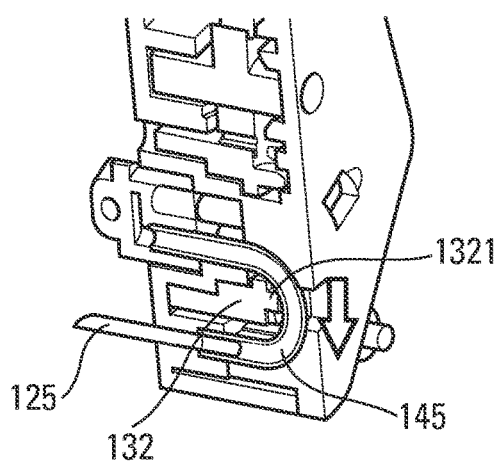
FIGS. 11 and 12 are diagrammatic and partially cut-away perspective views showing, in section, how the selector module in FIGS. 6 and 8 operates.
Figure 12:
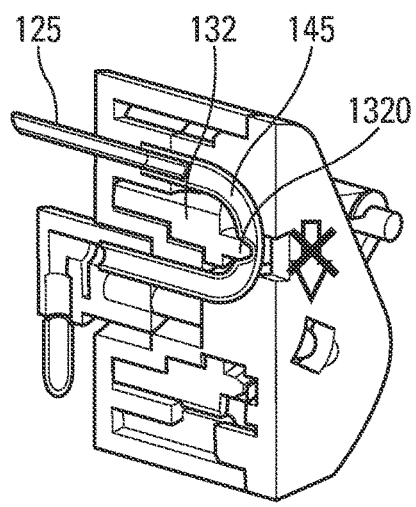

FIG. 11 shows a tube 145 that is not pinched, and consequently fluid can flow along said tube 145, whereas FIG. 12 shows a tube 145 that is pinched or flattened, and thus no fluid flow is possible.

Figure 16:
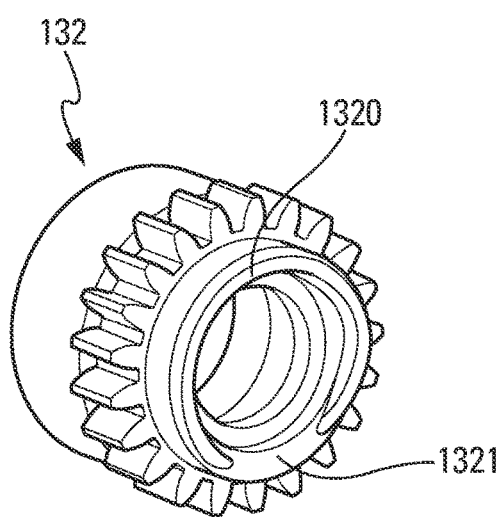
FIG. 16 is a diagrammatic perspective view of the selector ring of the selector module in FIGS. 6 and 8.
Figure 17:
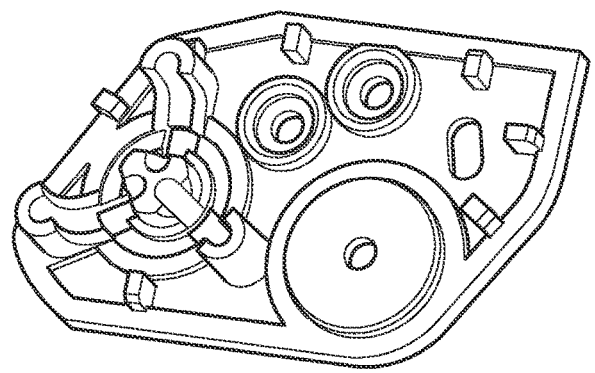
FIG. 17 is a diagrammatic and fragmentary perspective view of the rear portion of the selector module in FIGS. 6 and 8.
Figure 18:
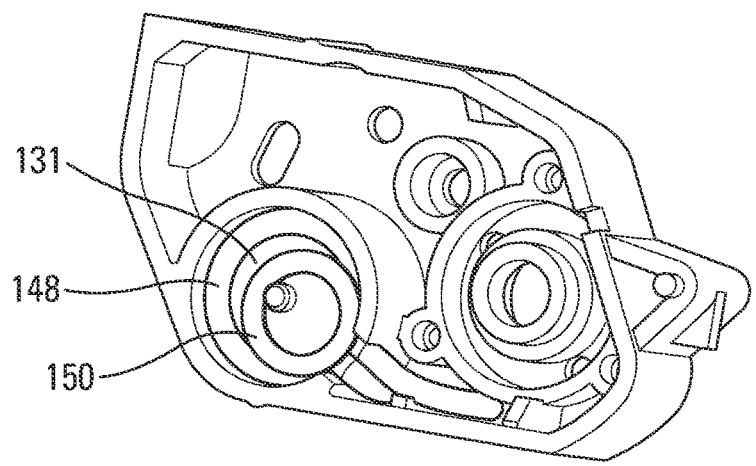
FIG. 18 is a diagrammatic and partially cut-away perspective view of a peristaltic pump in an advantageous embodiment.

In the example shown in FIGS. 11 to 16, a selector cog 132 that forms part of the cog system of the single rotary actuator 130, includes a cam 1320 that is formed by a projection that is circularly arcuate, said cam being interrupted by a gap 1321, as can be seen in FIG. 16. When the cam 1320 comes into contact with a tube 145 it pinches it so as to cut off the flow of fluid, whereas when the tube 145 is situated facing said gap 1321 flow is possible.

Figure 13:
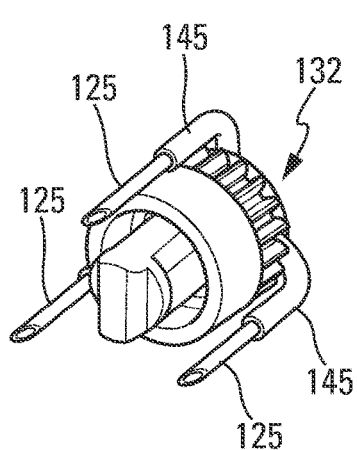
FIGS. 13 and 14 are diagrammatic and fragmentary perspective views showing the selector ring of the selector module in FIGS. 6 and 8, shown in front and rear views respectively.
Figure 14:
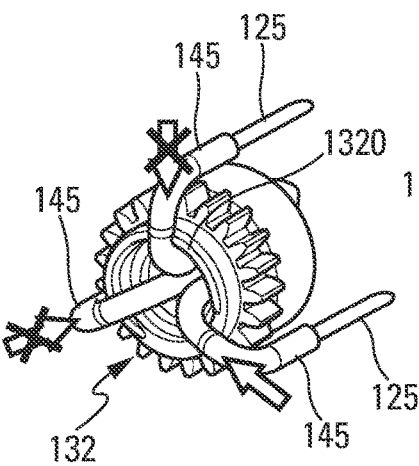

FIGS. 13 and 14 show an example in which two of the three tubes 145 are pinched, and a single tube 145 is "open". When the pump is actuated, the medication is sucked from the reservoir 210 that is connected to said open tube 145.

Naturally, other configurations are possible, as shown in FIGS. 27 to 41, which show other variant embodiments.

Figure 27:
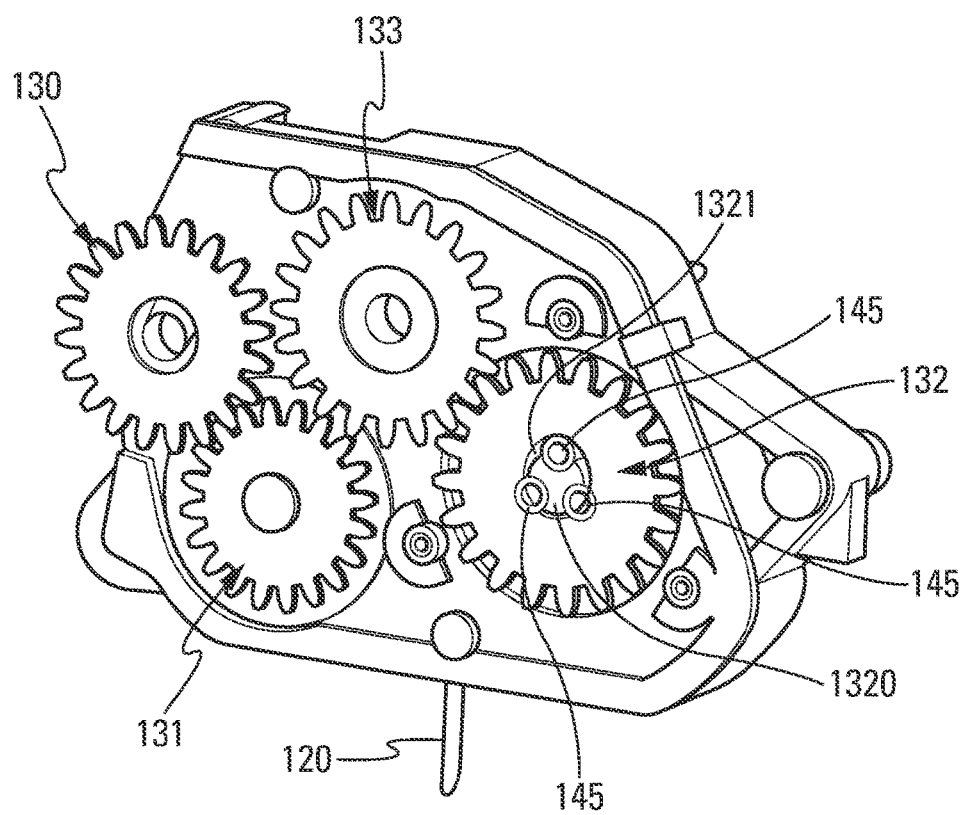
FIG. 27 is a diagrammatic and partially cut-away perspective view of the selector module in another advantageous embodiment.
Figure 28:
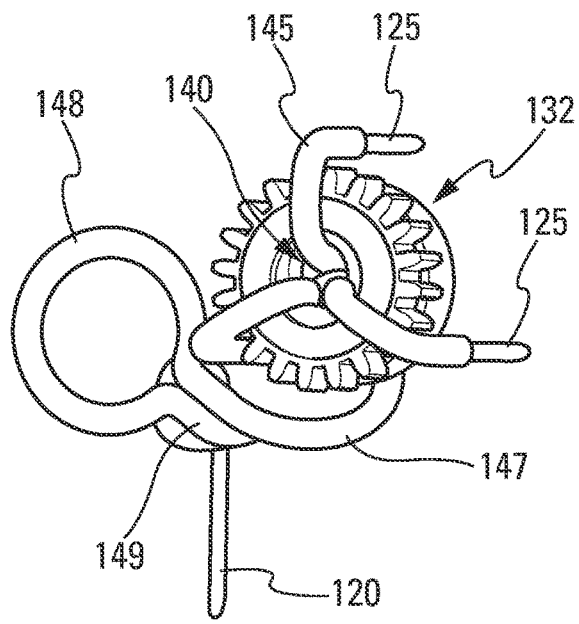
FIG. 28 is a diagrammatic and fragmentary perspective view of the tubing of the FIG. 27 selector module.
Figure 29:
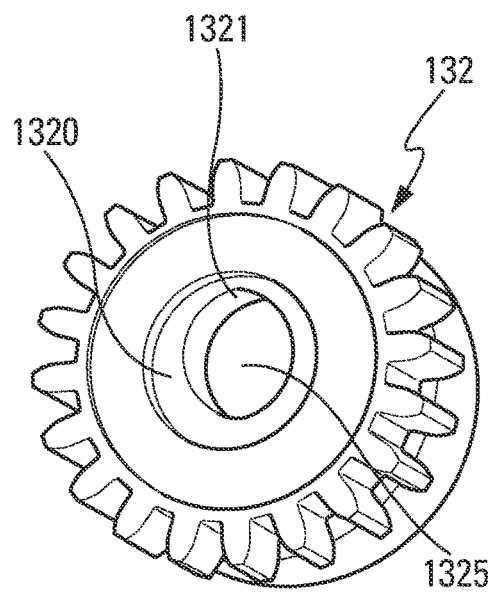
FIG. 29 is a diagrammatic and fragmentary perspective view of the selector ring of the FIG. 27 selector module.

Thus, in FIGS. 27 to 29, the cam 1320 is formed in radial manner in a central hole 1325 of the selector cog 132. The cam 1320 includes a larger-diameter portion 1321. The tubes 145, which are also three in number in this example, pass through the central hole 1325. When a tube 145 co-operates with the cam 1320 it is pinched, whereas when it co-operates with the larger-diameter portion 1321 it is not pinched.

FIGS. 30 to 37 show another embodiment. In this embodiment, the selector cog is replaced by a rotary selector shaft 135 that supports a plurality of cam elements 1350, specifically three in the example shown. A pinch member 1360 is provided between said cam elements 1350 and the tubes 145. The pinch member 1360 advantageously comprises flexible blades, one for each tube 145, which blades are resiliently deformed by the cam elements 1350 of the selector shaft 135. This avoids the cam elements rubbing against the tubes, which could have the drawback of deforming them and of making pinching less effective.

FIGS. 32 and 35 show a tube 145 that is not pinched, and consequently said tube 145 can pass a flow of fluid, whereas FIGS. 33 and 34 show a tube 145 that is pinched or flattened by a blade of the pinch member 1360, itself pushed by a cam element 1350 of the selector shaft 135, and thus no fluid flow is possible.

Figure 39:
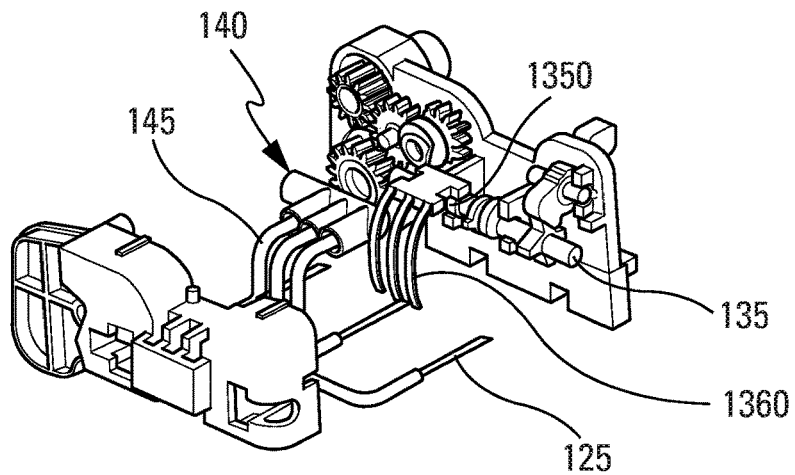
FIG. 39 is a diagrammatic and fragmentary exploded view in perspective of the FIG. 38 selector module.
Figure 40:
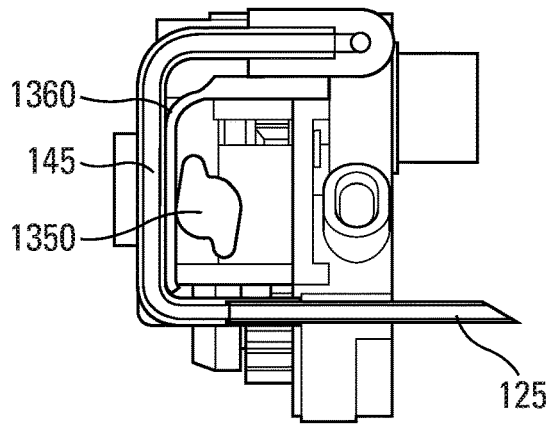
FIGS. 40 and 41 are diagrammatic and partially cut-away perspective views showing how the selector module in FIGS. 38 and 39 operates.
Figure 41:
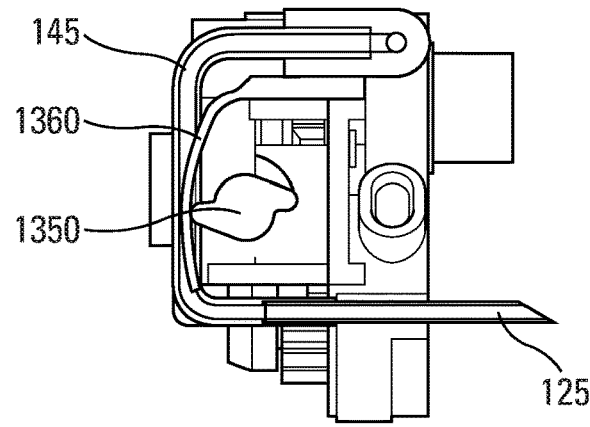

The example in FIGS. 38 to 41 is very similar to the embodiment in FIGS. 30 to 37, with the three reservoirs arranged side-by-side, as shown in FIG. 39 by the three priming needles 125 arranged in parallel manner in the same plane.

In the examples shown, the pinch member 1360 forms a single-piece part, but in a variant it is possible to envisage a plurality of separate pinch members, each formed by a flexible blade.

Figure 19:
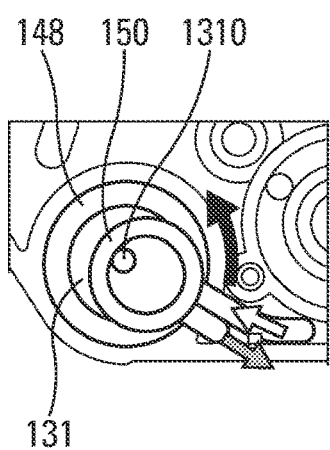
FIGS. 19 to 21 are diagrammatic section views showing how the FIG. 18 peristaltic pump operates.
Figure 20:
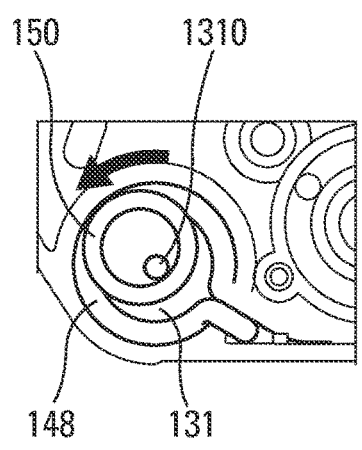
Figure 21:
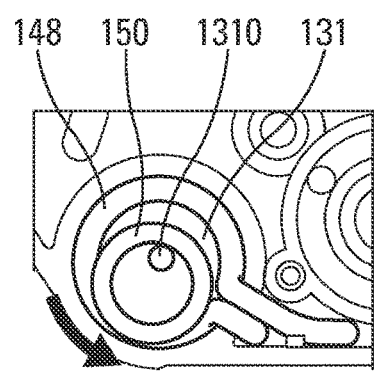
Figure 22:
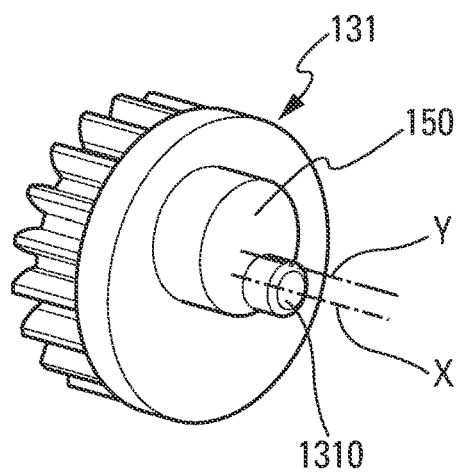
FIG. 22 is a diagrammatic perspective view of the crankshaft of the FIG. 18 peristaltic pump.
Figure 23:
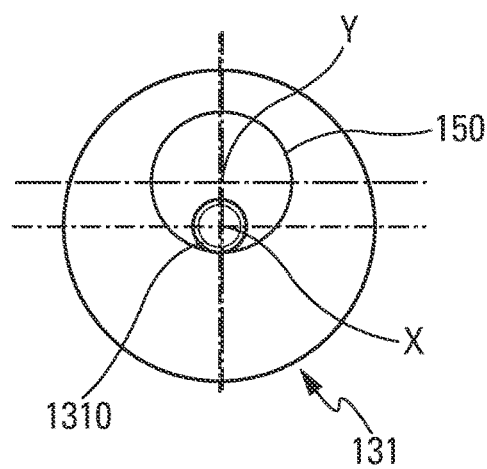
FIG. 23 is a diagrammatic section view of the crankshaft of the FIG. 18 peristaltic pump.
Figure 24:
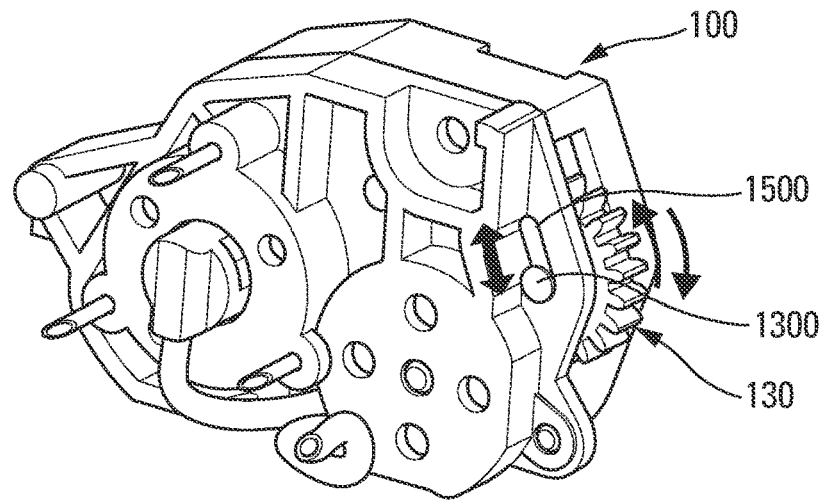
FIG. 24 is a diagrammatic and partially cut-away perspective view of the selector module in an advantageous embodiment.

The dispenser system preferably comprises a peristaltic pump. Said peristaltic pump comprises a ring 150 that turns on a crankshaft 131 about an axis of rotation Y that is offset relative to the axis of rotation X of said crankshaft 131. Preferably, and as can be seen in FIG. 22, the axis of rotation X of the crankshaft 131 is formed by a central axial cylinder 1310, about which the ring 150 can turn. A portion of tube 148 that goes from the manifold 140 to the injection needle 120 extends around said crankshaft 131, so that the ring 150, as it turns about its offset axis of rotation Y, turns about said central axial cylinder 1310 of the crankshaft 131, moving the compression along the tube 148, thereby causing the fluid that passes in said tube 148 to be dispensed. FIGS. 19 to 21 show how the peristaltic pump operates.

Once dispensing of the fluid has terminated, the injection needle 120 is retracted into the device, preferably automatically. The end of dispensing of the fluid can be identified by mechanical and/or software monitoring.

The embodiment shown in the figures shows a device that is adapted to include one, two, or three reservoirs 210. Provision may be made to use masks on the reservoir module 200, which masks are perforated/penetrated by the presence of the reservoir, during assembly of the device. When a reservoir is not present, its mask acts to seal the respective branch of the tubing, preventing medication from leaking during dispensing.

The above-described embodiment provides the following advantages in particular:
  the speed of dispensing the fluid may be adjusted so as to optimize individual treatments, and it may also vary over time; and
  the multiple reservoirs make it possible to use a combination of medications that can be dispensed at different speeds and at different moments.

The use of simultaneous or sequential injections may be applied in a system having a plurality of cartridges in order to:
  reduce the flowrate of fluid and ease the pain of the patient; and
  make it possible to improve the effectiveness of certain preparations of cocktails of medications.

The present invention is described above with reference to several advantageous embodiments and variants, but naturally any modification could be applied thereto by a person skilled in the art, without going beyond the ambit of the present invention, as defined by the accompanying claims.

The invention claimed is:

1. A fluid injection device comprising: a body for coming into contact with an injection site (SI); at least three fluid reservoirs; an injection needle for penetrating into said injection site (SI) so as to inject therein the contents of one or more reservoir(s); and a respective priming needle associated with each reservoir for penetrating into said reservoir before dispensing the fluid, each reservoir including a tube that is connected at one end to its priming needle, and at the other end to said injection needle; said device further comprises reservoir selector means for selecting one or more reservoirs, the contents of which are to be dispensed during the next actuation, said selector means comprising a rotary member that is provided with cam means that are adapted to co-operate with the tubes of the reservoirs so as to open or close the flow of fluid through each tube, the flow of fluid in each tube being closed off by said cam means pinching or flattening said tube, thereby selecting one or more of the reservoir to be dispensed during actuation;
  wherein said rotary member is a selector shaft provided with cam elements; and
  wherein said cam elements co-operate with a pinch member provided with a plurality of flexible blades, one for each reservoir tube, such that when a cam element deforms a flexible blade of the pinch member, said flexible blade pinches its respective tube so as to cut off the flow of fluid.

2. The device according to claim 1, wherein said pinch member is made as a single piece.

3. The device according to claim 1, including a peristaltic pump comprising a ring that is mounted to rotate on a crankshaft, said ring turning about an axis of rotation (Y) that is offset relative to the axis of rotation (X) of said crankshaft, progressively compressing a portion of tube that extends around said crankshaft.

4. The device according to claim 3, wherein said ring turns about a central cylinder of said crankshaft.

5. The device according to claim 3, wherein said portion of tube is connected at one end to a manifold that receives the tubes of each reservoir, and at the other end to said injection needle.

6. The device according to claim 1, wherein each reservoir has a fluid content in the range 1 mL to 10 mL.

7. The device according to claim 1, wherein said device includes an electronic module.

8. The device according to claim 7, wherein said electronic module comprises: a power supply; a microprocessor; storage means; signal transceiver means; and a motor.

9. The device according to claim 7, wherein said electronic module is reusable and is assembled in removable manner on the device.

10. The device according to claim 1, wherein each reservoir has a fluid content in the range of about 3 mL.

11. The device according to claim 8, wherein said power supply is a rechargeable battery.

12. A fluid injection device comprising: a body for coming into contact with an injection site (SI); at least three fluid reservoirs; an injection needle for penetrating into said injection site (SI) so as to inject therein the contents of one or more reservoir(s); and a respective priming needle associated with each reservoir for penetrating into said reservoir before dispensing the fluid, each reservoir including a tube that is connected at one end to its priming needle, and at the other end to said injection needle; said device further comprises reservoir selector means for selecting one or more reservoirs, the contents of which are to be dispensed during the next actuation, said selector means comprising a rotary member that is provided with cam means that are adapted to co-operate with the tubes of the reservoirs so as to open or close the flow of fluid through each tube, the flow of fluid in each tube being closed off by said cam means pinching or flattening said tube, thereby selecting one or more of the reservoir to be dispensed during actuation; and wherein the device further comprises a single rotary actuator that, when the single rotary actuator turns in a first direction of rotation, activates the selection of the reservoir(s) to be dispensed, and that, when the single rotary actuator turns in the opposite direction, actuates a dispenser system, in particular a peristaltic pump.

13. The device according to claim 12, wherein said rotary member is a selector cog provided with a cam.

14. The device according to claim 13, wherein said cam is formed by a projection that is circularly arcuate, said cam being interrupted by at least one gap, such that when said cam is in contact with a tube it pinches it so as to cut off the flow of fluid, and when a tube is situated facing said gap it is possible for fluid to flow.

15. The device according to claim 13, wherein said cam is formed in radial manner in a central hole of said selector cog, said tubes passing through said central hole, said cam including a larger-diameter portion and a smaller diameter portion, such that one of the tubes that co-operate with said smaller diameter portion is pinched, and one of the tubes that co-operate with the larger-diameter portion is not pinched.

16. The device according to claim 12, wherein said actuator includes a central pin that extends through an oblong opening of the body, thereby forming a floating cog.

17. The device according to claim 12, including a peristaltic pump comprising a ring that is mounted to rotate on a crankshaft, said ring turning about an axis of rotation (Y) that is offset relative to the axis of rotation (X) of said crankshaft, progressively compressing a portion of tube that extends around said crankshaft.

18. The device according to claim 17, wherein said ring turns about a central cylinder of said crankshaft.

19. The device according to claim 17, wherein said portion of tube is connected at one end to a manifold that receives the tubes of each reservoir, and at the other end to said injection needle.

20. The device according to claim 12, wherein each reservoir has a fluid content in the range 1 mL to 10 mL.

21. The device according to claim 12, wherein said device includes an electronic module.

22. The device according to claim 21, wherein said electronic module comprises: a power supply; a microprocessor; storage means; signal transceiver means; and a motor.

23. The device according to claim 21, wherein said electronic module is reusable and is assembled in removable manner on the device.

24. The device according to claim 12, wherein each reservoir has a fluid content in the range of about 3 mL.

25. The device according to claim 22, wherein said power supply is a rechargeable battery.

\* \* \* \* \*